United States Patent
Bannister et al.

(10) Patent No.: US 10,022,519 B2
(45) Date of Patent: Jul. 17, 2018

(54) MICRO-INFUSION DELIVERY SYSTEM

(71) Applicant: Boston Scientific Scimed, Inc., Maple Grove, MN (US)

(72) Inventors: Philip Bannister, Longford (IE); Brenda Clarke, Galway (IE); Gill Aoibheann, Galway (IE); Michelle Hannon, Galway (IE); Dwayne Noone, Galway (IE); Fengnan Fang, Dublin (IE); Emma Jane Mooney, Co. Galway (IE); John Kilcooley, Gort (IE); Javier Palomar-Moreno, Galway (IE); Aiden Flanagan, Co. Galway (IE); Tim O'Connor, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 247 days.

(21) Appl. No.: 14/997,156

(22) Filed: Jan. 15, 2016

(65) Prior Publication Data
US 2016/0206851 A1    Jul. 21, 2016

Related U.S. Application Data

(60) Provisional application No. 62/104,491, filed on Jan. 16, 2015.

(51) Int. Cl.
*A61M 25/00* (2006.01)
*A61B 5/042* (2006.01)
(Continued)

(52) U.S. Cl.
CPC ....... *A61M 25/0084* (2013.01); *A61B 5/0422* (2013.01); *A61B 5/6855* (2013.01);
(Continued)

(58) Field of Classification Search
CPC .......... A61M 25/0084; A61M 25/0152; A61M 25/065; A61M 25/0136; A61M 37/00;
(Continued)

(56) References Cited

U.S. PATENT DOCUMENTS 5,239,999 A * 8/1993 Imran ................. A61B 5/0422
600/374
6,162,203 A    12/2000 Haaga
(Continued)

FOREIGN PATENT DOCUMENTS

EP    2668923 A1    12/2013

*Primary Examiner* — Manuel Mendez
(74) *Attorney, Agent, or Firm* — Seager, Tufte & Wickhem, LLP

(57) ABSTRACT

An injection catheter system that includes (a) an actuator; (b) an outer needle comprising a sharp tip and a tubular body defining a lumen, and extending distally from the actuator; and (c) an inner needle at least partially disposed within the lumen and extending distally from the actuator, the inner needle having a distal tip configured such that at least a portion of the distal tip has a surface contour with an interstitial cavity adapted to receive a therapeutic gel. The system is configured such that (a) in a first position, the distal tip is fully disposed within the lumen to temporarily retain the therapeutic gel in the interstitial cavity and (b) in a second position, the outer needle is retracted proximally, exposing the interstitial cavity to deliver the therapeutic gel to a target area in a body.

19 Claims, 15 Drawing Sheets

(51) Int. Cl.
  *A61B 5/00*   (2006.01)
  *A61M 25/01*  (2006.01)
  *A61M 25/06*  (2006.01)
  *A61M 37/00*  (2006.01)
  *A61B 17/00*  (2006.01)
  *A61B 17/34*  (2006.01)
  *A61B 18/14*  (2006.01)

(52) U.S. Cl.
  CPC ..... *A61B 17/3478* (2013.01); *A61M 25/0136* (2013.01); *A61M 25/0152* (2013.01); *A61M 25/065* (2013.01); *A61M 37/00* (2013.01); *A61B 17/3468* (2013.01); *A61B 18/1492* (2013.01); *A61B 2017/00247* (2013.01); *A61B 2017/00685* (2013.01); *A61B 2017/3458* (2013.01); *A61M 2025/0085* (2013.01); *A61M 2025/0089* (2013.01); *A61M 2025/0175* (2013.01)

(58) Field of Classification Search
  CPC .. A61M 2025/0085; A61M 2025/0089; A61M 2025/0175; A61B 5/0422; A61B 5/6855; A61B 17/3478; A61B 17/3468; A61B 17/32002; A61B 17/3415; A61B 18/1492; A61B 2017/00247; A61B 2017/00685; A61B 2017/3458
  USPC .............. 606/167; 604/93.01, 164.06; 607/3; 600/374
  See application file for complete search history.

(56) References Cited

U.S. PATENT DOCUMENTS

| | | | |
|---|---|---|---|
| 6,517,519 B1* | 2/2003 | Rosen ................ | A61B 17/3415 604/164.06 |
| 6,749,617 B1* | 6/2004 | Palasis ............... | A61B 17/3468 606/167 |
| 2004/0068299 A1* | 4/2004 | Laske ............... | A61M 25/0082 607/3 |
| 2004/0199120 A1 | 10/2004 | Lohr et al. | |
| 2006/0253069 A1* | 11/2006 | Li .................... | A61B 17/32002 604/93.01 |

* cited by examiner

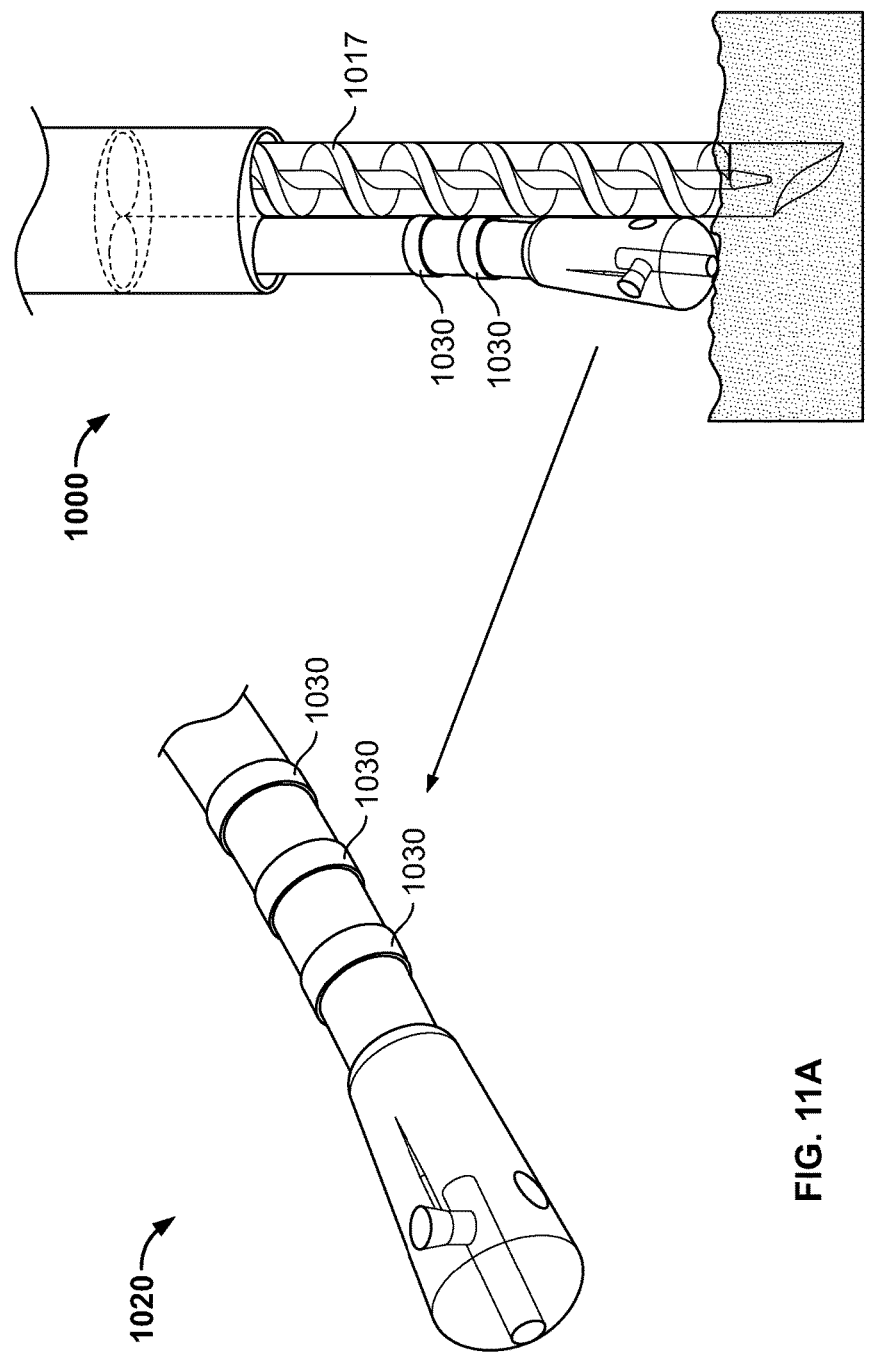

MICRO-INFUSION DELIVERY SYSTEM

CROSS-REFERENCE TO RELATED APPLICATIONS

This application claims priority under 35 U.S.C. § 119(e) to U.S. Provisional Application Ser. No. 62/104,491, filed on Jan. 16, 2015, entitled "Micro-Infusion Delivery System," the entire contents of which are hereby incorporated by reference herein.

TECHNICAL FIELD

This invention relates to delivering a therapeutic gel to a target area in a patient's body such as cardiac tissue.

BACKGROUND

Heart failure due to damaged cardiac tissue is a significant health care issue. It has been proposed to treat the damaged tissue directly with a therapeutic agent designed to help regenerate the damaged tissue. An example of a therapeutic agent proposed for this use is stem cells. The stem cells would be delivered in the form of a gel to the site of the damaged tissue. The gels, however, have relatively high viscosities. Therefore, administering the gel through a conventional syringe would subject the stem cells to relatively high pressure, potentially damaging the cells and compromising their therapeutic efficacy.

SUMMARY

Methods, devices, and systems provided herein can deliver therapeutics, such as a gel including stem cells, to a treatment location. In some cases, methods, devices, and systems provided herein can deliver gels including stem cells without compromising their therapeutic efficacy. In some cases, methods, devices, and systems provided herein can deliver gels including stem cells with a limited amount of shear force exerted on the stem cells.

In a first aspect, there is described an injection catheter system that includes (a) an actuator; (b) an outer needle that extends distally from the actuator and comprises a sharp tip and a tubular body defining a lumen; and (c) an inner needle at least partially disposed within the lumen and extending distally from the actuator. The inner needle has a distal tip configured such that at least a portion of the distal tip has a surface contour with an interstitial cavity adapted to receive a therapeutic gel. The system is configured such that (a) in a first position, the distal tip is fully disposed within the lumen to temporarily retain the therapeutic gel in the interstitial cavity and (b) in a second position, the outer needle is retracted proximally, exposing the interstitial cavity to deliver the therapeutic gel to a target area in a body. The actuator is adapted to proximally or distally translate the outer needle such that translation of the outer needle is independent of translation of the inner needle.

In some implementations, the surface contour may have a spiral configuration, helical configuration, non-cylindrical configuration, cross-shaped configuration, or tapered cylindrical configuration. The inner needle may include a tubular body defining an inner lumen that is adapted to receive a wire (e.g., a core wire, guide wire, or plug).

In some implementations, the system may include an outer sheath having a sheath lumen there through. A reservoir may be disposed within the sheath lumen, whereby the reservoir is adapted to receive a plurality of encapsulated forms of the therapeutic gel. The encapsulate forms maybe generally spherical shaped polymeric vesicles having a cavity filled with the therapeutic gel. The reservoir may include a piston adapted to release the therapeutic gel from the polymeric vesicle and deposit the therapeutic gel in the interstitial cavity of the distal tip of the inner needle.

In some implementations, the system may further include a lead assembly disposed within the sheath lumen. The lead assembly includes (a) an elongate body with a proximal end portion and a distal end portion having a tip, and (b) a plurality of electrodes disposed about the distal end portion for locating the tip within a patient's body. The actuator is adapted to proximally or distally translate the lead assembly such that translation of the lead assembly is independent of the translation of both the outer need and inner needle. In some implements, the system may further include a revolving cylinder containing multiple chambers in the sheath lumen and at least one injection barrel for loading therapeutic gel from the multiple chambers to the interstitial cavity in the inner needle. In some implementations, the target area may be cardiac tissue, (e.g., the myocardium).

In one particular implementation, the target tissue is cardiac tissue and the distal tip of the inner needle has a tapered, spiral shape with a spiral interstitial cavity for retaining the therapeutic gel.

In another aspect, there is described an injection catheter system that includes a helical ridge wrapped around a cylindrical core and at least one actuator adapted to advance and retract the helical ridge and the cylindrical core. The helical ridge being adapted to receive a therapeutic gel between adjacent portions of the ridge. The cylindrical core and/or the helical ridge can have a sharp distal end to facilitate insertion of the helical ridge, cylindrical core, and any therapeutic gel retained between adjacent portions of the ridge into a target tissue. The actuator can be adapted to retract the helical ridge by rotating the helical ridge during retraction such that the helical ridge unscrews from engagement with any therapeutic gel retained between adjacent portions of the ridge and thus remains in the target tissue. In some cases, the helical ridge and the cylindrical core are retracted simultaneously. In some cases, the helical ridge and the cylindrical core are a unitary structure. In some cases, the helical ridge and the cylindrical core are adapted to be retracted independently of each other. In some cases, the cylindrical core is adapted to be retracted with different rotation characteristics than the helical ridge. In some cases, the combination of a helical ridge, a cylindrical core, and therapeutic gel between adjacent portions of the ridge can be inserted without an accompanying outer needle without experiencing damaging shear forces on the therapeutic gel. For example, in some cases a system lacking an accompanying outer needle can include a helical ridge having a convex surface facing direction of entry adapted to snagging on tissue.

In another aspect, there is described a method for using the above-described injection system to deliver a therapeutic gel to cardiac tissue. The method includes penetrating the cardiac tissue with the injection catheter; delivering the therapeutic gel to the cardiac tissue by proximally retracting the outer needle using the actuator to expose the therapeutic gel temporarily retained in the interstitial cavity to the cardiac tissue; and releasing the therapeutic gel into the cardiac tissue by retracting the inner needle from the cardiac tissue.

The injection catheter system delivers therapeutic gels having relatively high viscosities directly and accurately to a target site (e.g., damaged cardiac tissue) without subjecting the gels to forces that could damage the therapeutic agent and impair its efficacy. The gel can be pre-loaded in the injection catheter system or loaded by a physician at the time of use. The system can be used to deliver a single dose at a target site. Alternatively, the system can be used to deliver multiple doses at either a single site or multiple sites without re-loading.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 10, 11A, and 11B depict an example of an injection system provided herein having electrophysiology mapping capabilities.

Like reference symbols in the various drawings indicate like elements.

DETAILED DESCRIPTION

Figure 1A:
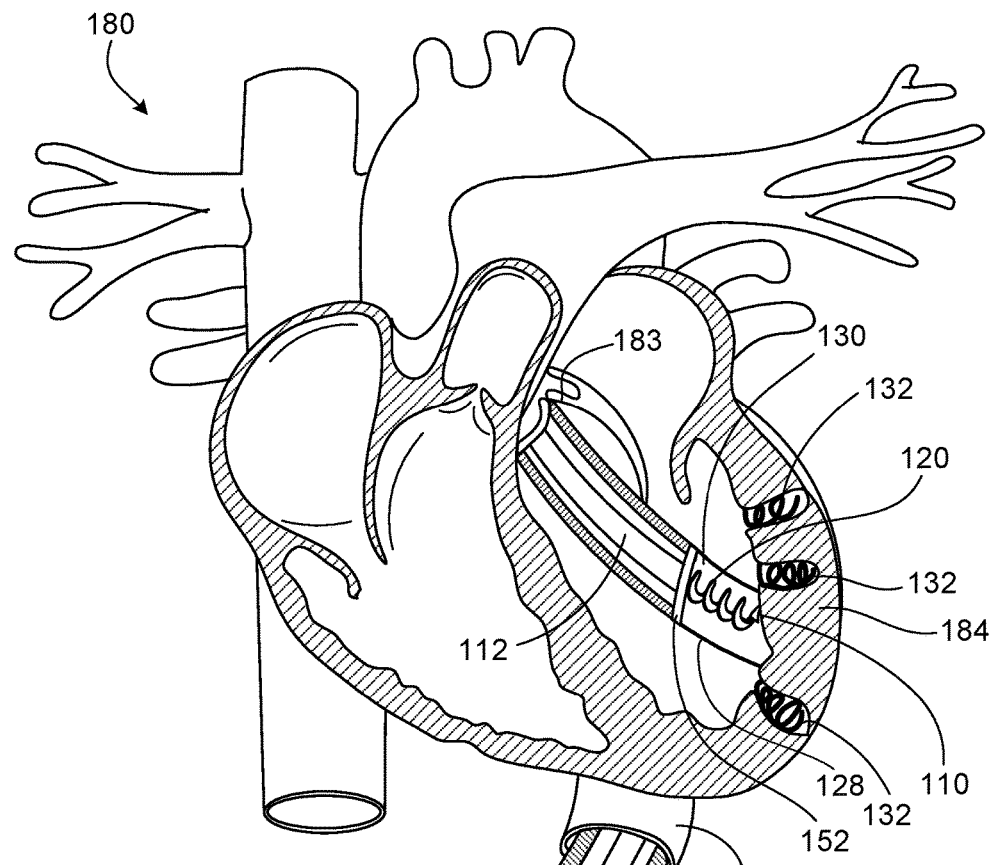
FIG. 1A illustrates how an injection catheter system provided herein might be used to deliver gels including stem cells to a treatment location.
Figure 1A:
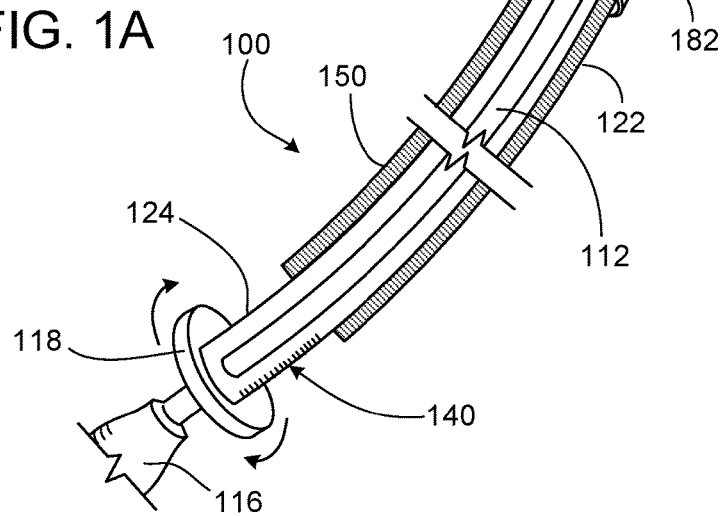
Figure 1B:
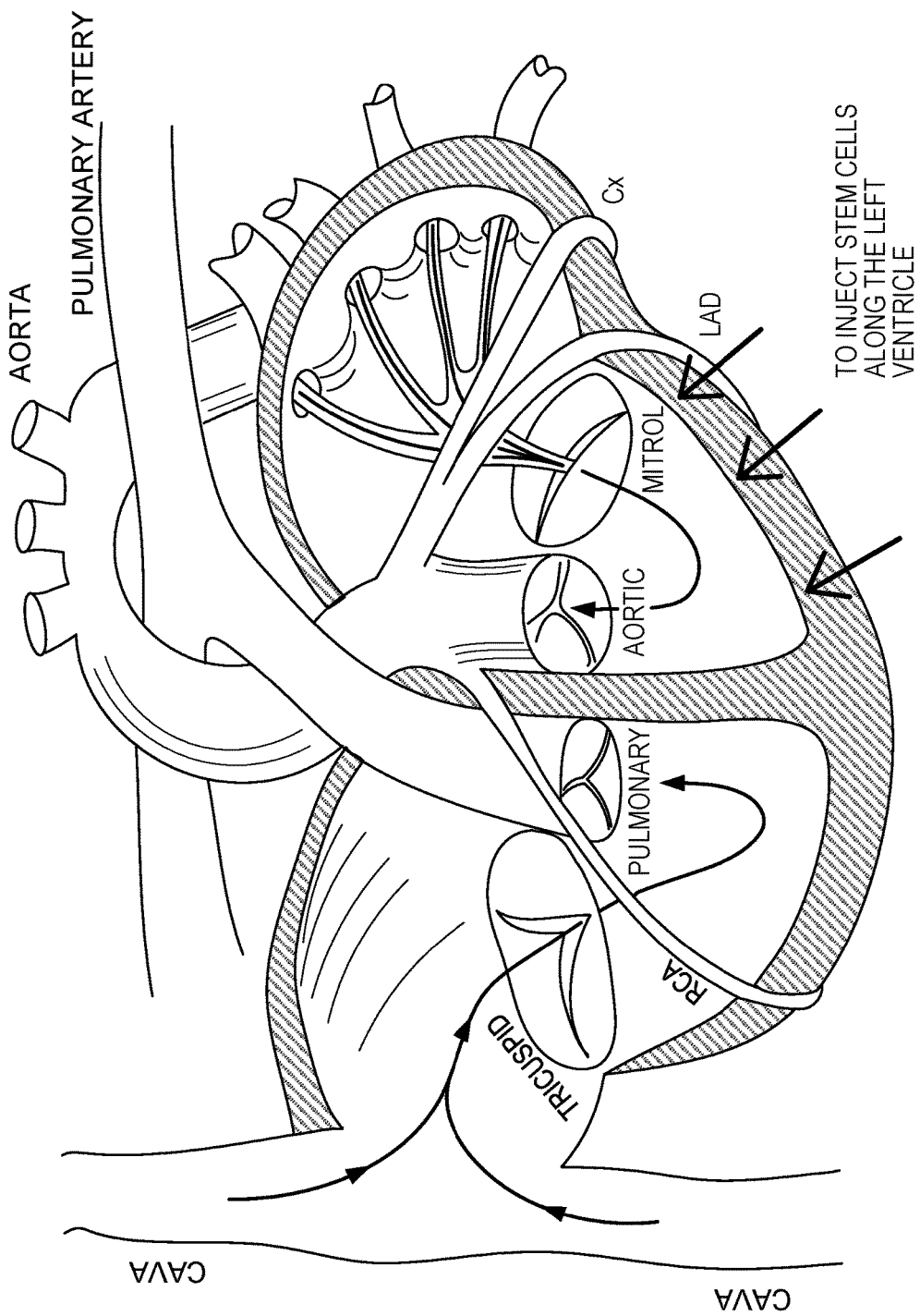
FIG. 1B illustrates positions where an injection catheter system provided herein can be used to deliver gels in methods provided herein.
Figure 2:
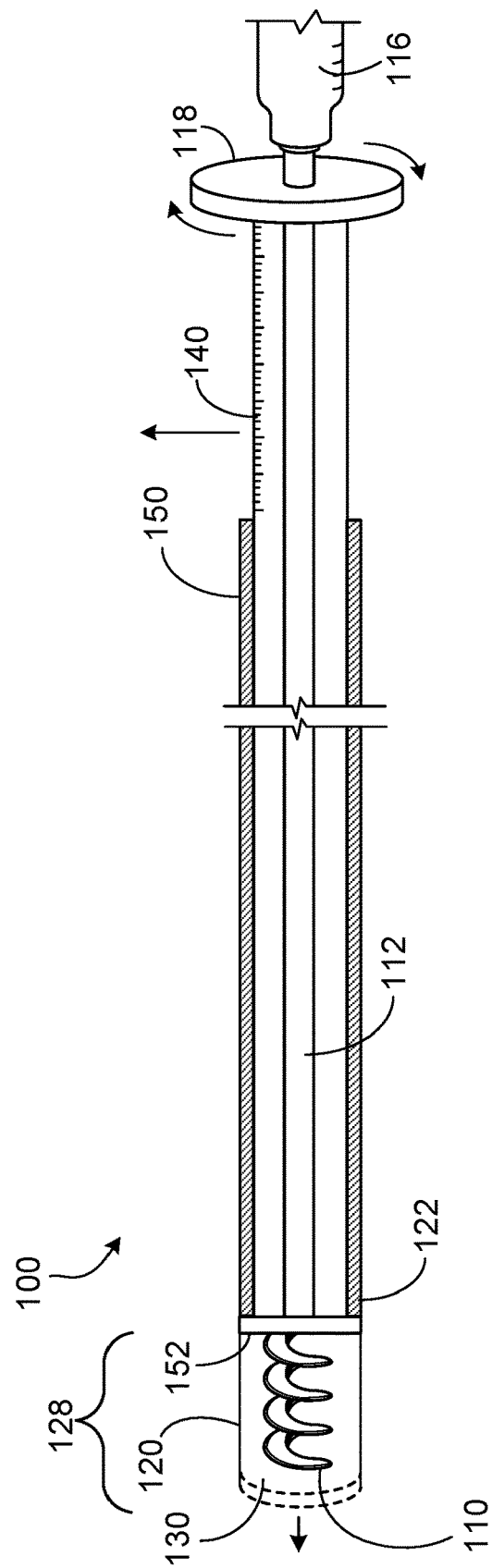
FIG. 2 illustrates an injection catheter system of FIG. 1A in greater detail.

Methods, devices, and systems provided herein can deliver therapeutics, such as gels including stem cells, to a treatment location, such a wall of a heart. FIG. 1 illustrates how methods, devices, and systems provided herein can be used to deliver therapeutic agent deposits 132 to a left ventricle wall 184 of a heart 180 by advancing an injection catheter system 100 through the aorta 182 and the aortic semilunar valve 183. FIG. 2 depicts the catheter system shown in FIG. 1A in greater detail. As shown, the injection catheter system 100 includes at least an inner member 112 including a distal end having an inner needle 110 and an outer member 122 having a distal end having an outer needle 120. Although inner needle 110 is illustrated in FIG. 1 as a simple spiral, inner needle 110 can have a solid spiral, such as those depicted in FIGS. 3A-3D and 4. The advancement and retraction of the inner needle 110 and outer needle 120 can be controlled using handle 116. The rotation of inner needle 110 can be controlled using rotation knob 118. Inner member 112 and outer member 122 can be positioned within a guide catheter 150. Examples of other handle systems are depicted in FIGS. 8A-8C and FIG. 9.

In use, for example, a distal tip 128 of catheter system 100 depicted in FIG. 1 can be positioned against the left ventricular wall 184. A distal end 152 of guide catheter 150 can have radiopaque elements used to ensure that it abuts heart wall 184. Once the guide catheter 150 is positioned adjacent to a treatment location, the combination of the inner member 112 and outer member 122 can be advanced using handle 116 to pierce into heart wall 184. Markings 140 along a proximal end 124 of outer member 122 can be used to show how deep the inner needle 110 and outer needle 120 advance into heart wall 184. After the needles advance, outer needle 120 can be retracted relative to inner needle 110 so that a therapeutic (such as a therapeutic gel 130) around the inner needle is remains in a resulting cavity. In some cases, a lever (not shown) on handle 116 connects with outer needle 120 via a rod such that outer needle 120 can be advanced or retracted by moving the lever back and forwards. In some cases, outer needle 120 can be connected with a hypotube (not shown) that extends proximally to handle 116 where it ends in a ring (not shown) outside the central part of handle 116 and the ring can be slid back and forth causing outer needle 120 at the distal end to move back and forth. Inner needle 110 can then be removed from the therapeutic gel 130 by simultaneously rotating and retracting inner needle 110. The rotation of inner needle 110 can be controlled by a rotation element at a proximal end of the catheter system 100.

Clinicians can deliver therapeutic agent deposits 132 to treatment locations in a patient using methods, systems, and devices provided. For example, a clinician can use a fluoroscopy or transesophageal ultrasonography that is connected to a video monitor to partially visualize a treatment location (e.g., the left ventricle). In some cases, an electrophysiology device (e.g., INTELLA, RHYTHMIA) can be used to monitor electrical activity on the ventricular wall and guide the delivery system to a site of low activity, which can identify damaged wall tissue for stem cell injection. In some cases, radiopaque marker bands can be implanted with the stem cells to ensure stem cells are implemented into the tissue wall of the heart. In some cases, when a clinician has positioned distal tip 128 against an inside surface of the left ventricular wall, the clinician can activate a catheter system 100 to deliver therapeutics 132. Thereafter, catheter system 100 can be removed. FIG. 1B depicts exemplary locations where stem cells may be injected along the left ventricle.

Referring now to FIG. 2, catheter system 100 includes an actuator (e.g., handle 116), a sheath 150 (which may also be referred to as a guide catheter), an outer member 122 having an outer needle 120 at a distal end, and an inner member 112 having an inner needle 110 at a distal end. Sheath 150, outer member 122, and inner member 112 each extend distally from handle 116. Sheath 150 and outer member 122 are each tubular. Inner member 112 is at least partially located within the tubular interior of outer member 122. Outer member 122, in turn, is at least partially located within the tubular interior of sheath 150.

Sheath 150 can include a tubular polymeric or metallic material. For example, in some cases, sheath 150 can be made from polymeric materials such as, but not limited to, polytetrafluoroethylene (PTFE), fluorinated ethylene propylene (FEP), Hytrel®, nylon, Picoflex®, Pebax®, and the like. In some cases, sheath 150 can be made from metallic materials such as, but not limited to, nitinol, stainless steel, stainless steel alloys, titanium, titanium alloys, and the like.

Distal tip 128 as shown in FIGS. 1 and 2 includes an outer needle 120 having a sharp distal edge to facilitate the piercing of distal tip 128 into a treatment location. Outer needle 120 can comprise a tubular metallic material. For example, in some cases, outer needle 120 can be made from metallic materials such as, but not limited to, nitinol, stainless steel, stainless steel alloys, titanium, titanium alloys, and the like. Outer needle 120 can be made in a variety of sizes to suit different applications. For example, in some cases a 19 gauge hypo tubing material is used to make outer needle 56. In other cases, a 22 gauge, 25 gauge, or 27 gauge hypo tubing material is used to make outer needle 120. Other larger or smaller sizes of tubing materials may also be used in some implementations. In some cases, the distal end portion of outer needle 120 can be beveled to create a sharp tip for penetrating tissue as outer needle 120 is axially translated in a distal direction along with inner needle 110. In some cases, outer needle 120 can include other styles of sharp distal end portions. In some cases, outer needle 120 is a hypodermic needle. In some cases, outer needle 120 has a non-coring tip.

Inner needle 110 and inner member 112 can include a polymeric, metallic, or composite material. For example, in some cases, inner needle 110 can be made from metallic materials such as, but not limited to, nitinol, stainless steel, stainless steel alloys, titanium, titanium alloys, platinum, composite materials, and the like. The size of the outer diameter of inner member 112 can be selected to complement or correspond to the size of the inner diameter of outer member 122. In some cases, a clearance therebetween of about 0.0005 inches (about 0.013 millimeters) per side is desirable. In some cases, a clearance therebetween in a range of about 0.000 inches to about 0.001 inches (about 0.000 millimeters to about 0.0254 millimeters) per side is desirable. In some cases, a clearance therebetween in a range of about 0.0005 inches to about 0.002 inches (about 0.013 millimeters to about 0.051 millimeters) per side is desirable. In some cases, a clearance therebetween in a range of about 0.001 inches to about 0.004 inches (about 0.025 millimeters to about 0.102 millimeters) per side is desirable.

Inner needle 110 has a generally spiral shape. In some cases, while inner needle 110 is spirally shaped, the portions of inner needle that are proximal of the distal end portion comprise a flexible cylindrical shaft member. In some cases, the distal end portion of inner needle 110 is a generally helically-shaped spiral. Such spiral shapes facilitate the removal of inner needle 110 from the therapeutic gel 132 as inner needle 110 is simultaneously rotated and translated axially. In addition, the interstitial space between the spirals allows tissue material to accumulate and be retained therein, thereby collecting sample tissue material in the needle biopsy system.

In some cases, distal end portion 128 of catheter system 100 includes an outer needle 120 and an inner needle 110 that have unique designs for penetrating and shearing tissue. In some cases, outer needle 120 can be configured with dual penetrating tips and serrated edges. Such a configuration can, for example, enhance penetration and shearing of tissue while substantially maintaining the cellular architecture of the tissue. Outer needle 120 can have a wide variety of configurations, which are envisioned within the scope of this disclosure.

Inner needle 110 can be configured as a coil. In some cases, a very distal tip of the coil can be a sharp point for facilitating penetration of tissue. In use, inner needle 110 simultaneously rotates and translates distally with a screw-like motion. The rotation and translational motion of inner needle 110 can substantially match the pitch of the coil of inner needle 110. Therefore, the coil interacts with the therapeutic gel 130 in a substantially uniform helical path as the coil is removed from the therapeutic gel 130. That helical path substantially matches the coil's shape. This configuration of inner needle 110, and the motion thereof, can thereby limit the shearing of the therapeutic gel 130 while substantially maintaining the cellular architecture of the tissue.

Injection catheter system 100 can include a therapeutic gel 130 loaded onto distal tip 128 between the inner needle 110 and outer needle 120. In some cases, therapeutic gel 130 can be loaded by dipping inner needle 110 into a gel solution including a therapeutic. In some cases, the therapeutic can include stem cells. Examples of suitable stem cells can include, but are not limited to, mouse, rat, porcine, bovine, or human stem cells. Various cell types suitable for the therapeutic gel 130 provided herein include, but are not limited to skin fibroblasts, cardiac fibroblasts, adult mesenchymal cells, human foetal lung fibroblasts (IMMO), stem cells (e.g., embryonic stem cells, or induced pluripotent stem cells for cell differentiation), and cancer cells (e.g., DU145 (prostate), C32 (melanoma), and A541 (lung) for cell-based protein or antibody therapies).

The therapeutic may include chemotherapeutic agents, in some cases. Examples of suitable chemotherapeutic agents include, but are not limited to, paclitaxel, camptothecin, daunorubicin, doxorubicin, idarubicin, amrubicin, pirarubicin, epirubicin, mitoxantrone, etoposide, teniposide, vinblastine, vincristine, mitomycin C, docetaxel, actinomycin D, colchicine, topotecan, irinotecan and gemcitabine, verapamil, valspodor, biricodar, quinidine, terfenadine, pervilleine A, or combinations thereof. Chemotherapeutic agents provided herein may be delivered as the therapeutic gel into solid tumors to treat various human tumors.

In some cases, the therapeutic can include nanoparticles. The nanoparticles can contain solid or hollow metallic materials that include, but are not limited to, gold and copper. In some cases, the nanoparticles can be used for tissue or cell ablation, or for inducing cell apoptosis by, for example, injecting the nanoparticles into targeted tissue and heating the nanoparticles within the targeted tissue. Nanoparticles can be discretely delivered into cancerous tissue, and thermally heated by an optical (e.g., light) or acoustic (e.g., radiofrequency) source to decrease the viability of cancers cells in a patient.

In some cases, the therapeutic can include a nucleic acid, which becomes incorporated into the cells of the particular tissue area that was targeted. The nucleic acid can include a polynucleotide molecule of covalently-bonded nucleotide monomers, i.e., a deoxyribonucleotide or ribonucleotide polymer in either single- or double-stranded form, which can include analogs of natural nucleotides. The nucleic acid can, in some cases, include natural, synthetically-prepared, modified (e.g., a nucleic acid derivative), and enzymatically-treated nucleic acids. Examples of nucleic acids can include, but are not limited to, DNA and RNA, modified DNA and RNA, antisense oligonucleotides, antisense iRNA (immune ribonucleic acid), ribozymes, siRNA (small/short interfering RNA), and shRNA (small/short hairpin RNA). The nucleic acid can be a part of a plasmid, a phage, a cosmid, and episome, or an integratable DNA fragment. The nucleic acid used to treat tissue can be isolated from a variety of sources, genetically engineered, amplified, and/or expressed/generated recombinantly, or chemically synthesized in vitro.

The therapeutic gel provided herein can be injected into various targeted treatment site, e.g., in necrotic or damaged tissue, a tumor site, or a tissue area in which revascularization is desired.

Figure 3A:
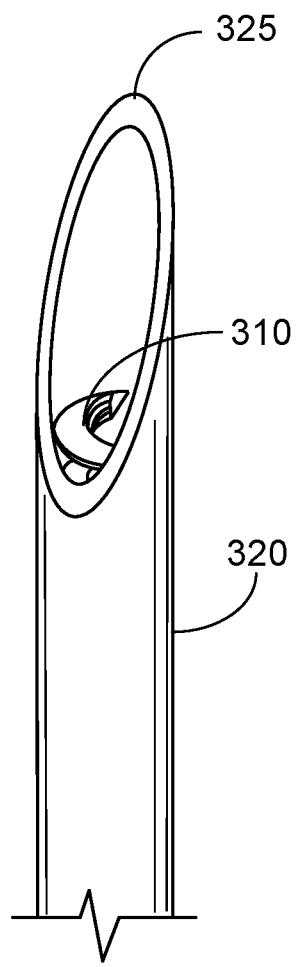
FIGS. 3A-3D are perspective views of various embodiments of a distal tip of an injection catheter system provided herein. Each distal tip includes a spiral contour and a hollow core.
Figure 3B:
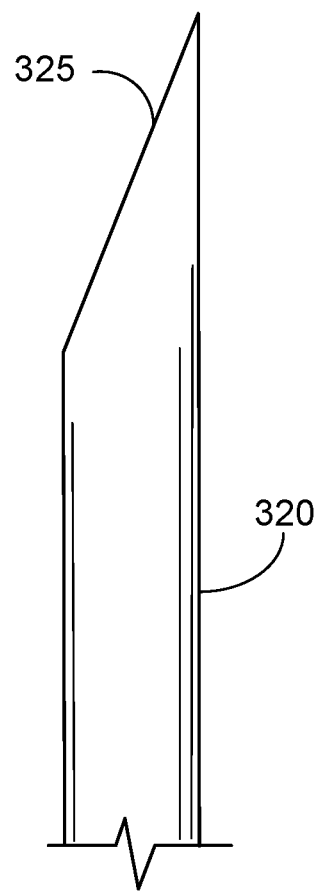
Figure 3C:
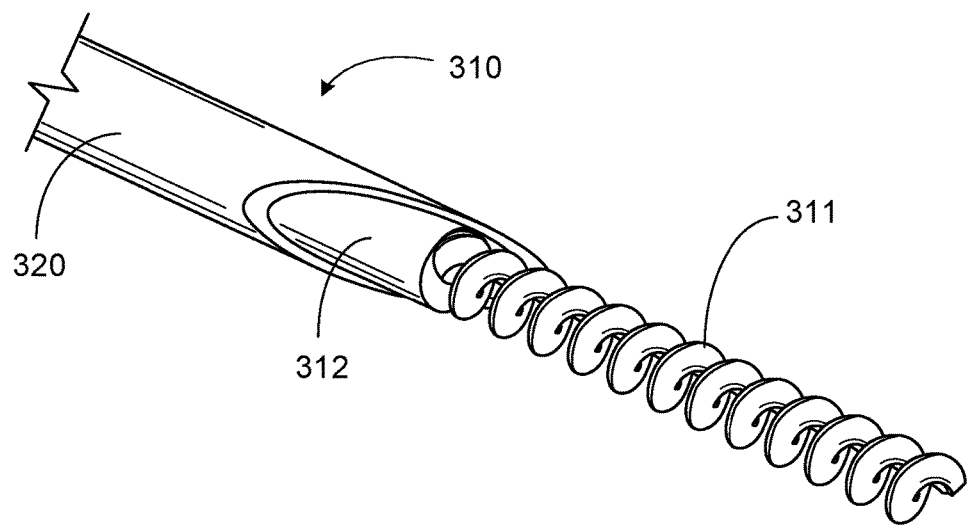
Figure 3D:
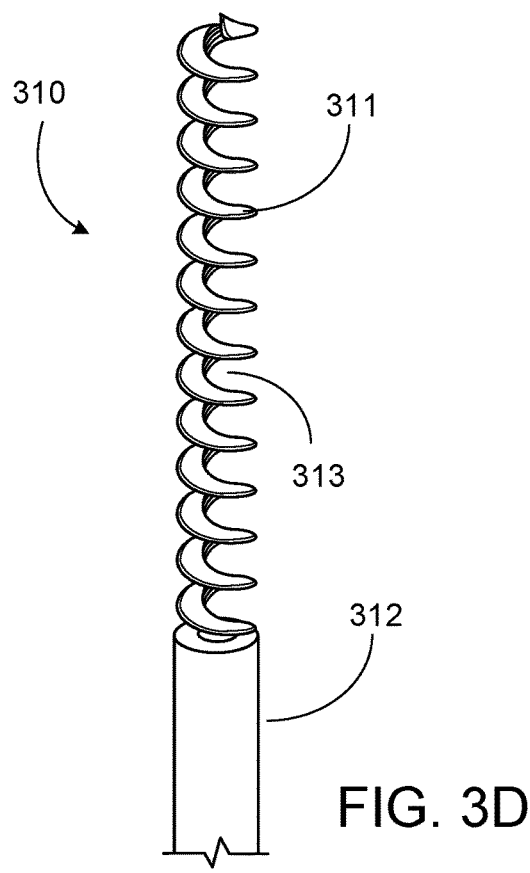

FIGS. 3A-3D depict an embodiment of a distal tip, which can be used as distal tip 128 in FIGS. 1 and 2. FIG. 3A shows inner needle 310 held within outer needle 320. As shown in FIGS. 3A and 3B, outer needle 320 includes a tapered opening 325 to facilitate a puncture into a treatment site. In some cases, outer needle 320 is a hypodermic needle. FIG. 3C depicts the distal tip of FIGS. 3A and 3B with outer needle 320 retracted relative to inner needle 310 to expose spirals 311 located at a distal section of an inner member 312. Therapeutic gel (not shown) can reside between adjacent spirals, such that the therapeutic gel becomes exposed when outer needle 320 is retracted. FIG. 3D depicts outer needle 320 in greater detail. Outer needle 320 of FIG. 3D has spirals 311 with a hollow core 313 at the distal section of inner member 312. Hollow core 313 can also be filled with therapeutic gel (not shown).

Figure 4A:
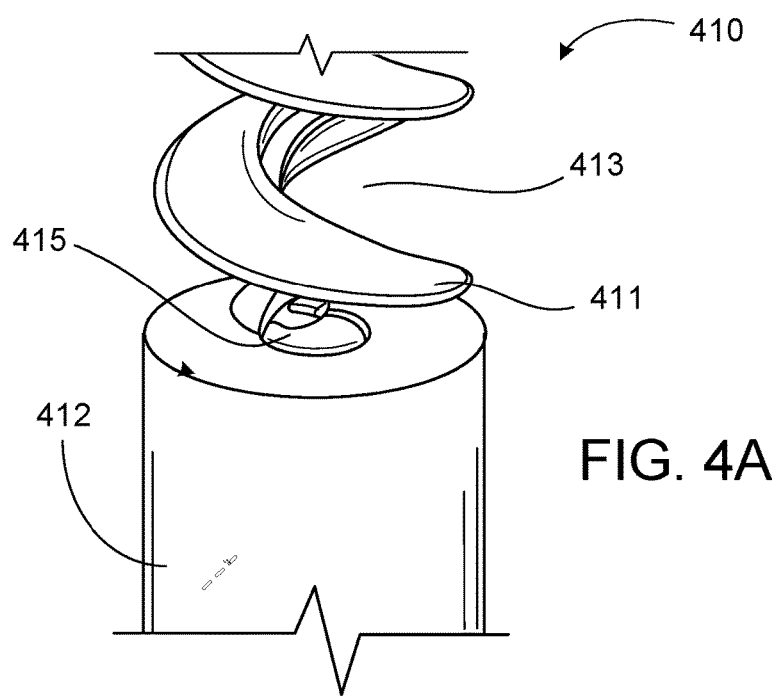
FIGS. 4A and 4B are perspective views of a second embodiment of a distal tip of an injection catheter system having a distal tip with a spiral contour and a solid core.
Figure 4B:
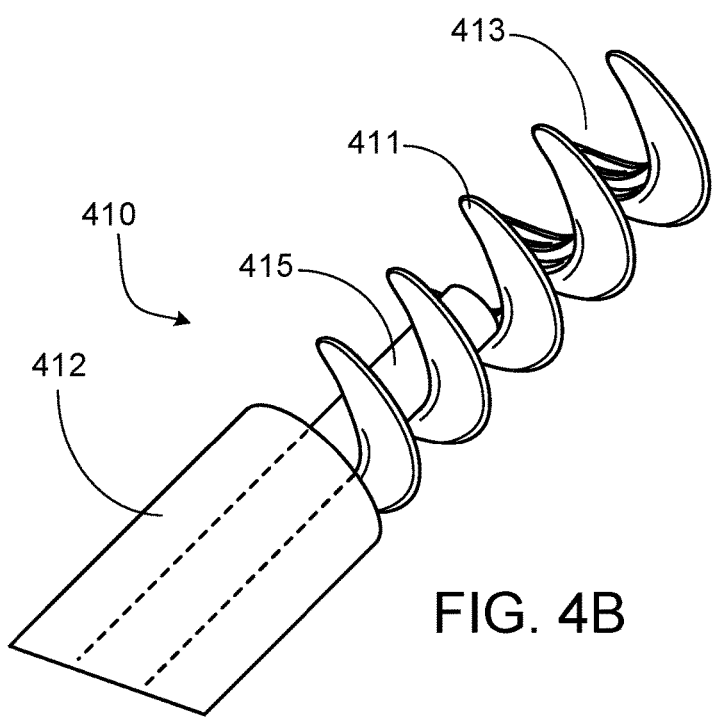

FIGS. 4A and 4B depict embodiments of an inner needle 410 of an inner member 412 including a guidewire 415 extending axially within inner member 412 and adapted to be moved relative to the inner needle 410. As inner needle 410 is rotated and retracted to remove the inner needle 410 from a deposit of therapeutic gel (not shown), a portion of guidewire 415 can move into the hollow core 413 to help counter frictional forces between the therapeutic gel and the spirals 411. In some cases, guidewire 415 can include grooves (not shown) that correspond to spirals 411. In some cases, a guidewire embodiment can be use with an outer member and an outer needle. In some cases, a guidewire embodiment can be used without an outer member or outer needle. Guidewire 415 is held in position while inner needle 410 is rotated clockwise, causing it to travel proximally down the spiral groove of guidewire 415. Guidewire 415 forces the therapeutic gel out of the hollow core of inner needle 410, thereby causing it to be retained at the treatment site. Following deposition, inner needle 410 can be rotated counterclockwise and back into outer needle (not shown), which is then withdrawn from the patient.

Figure 5:
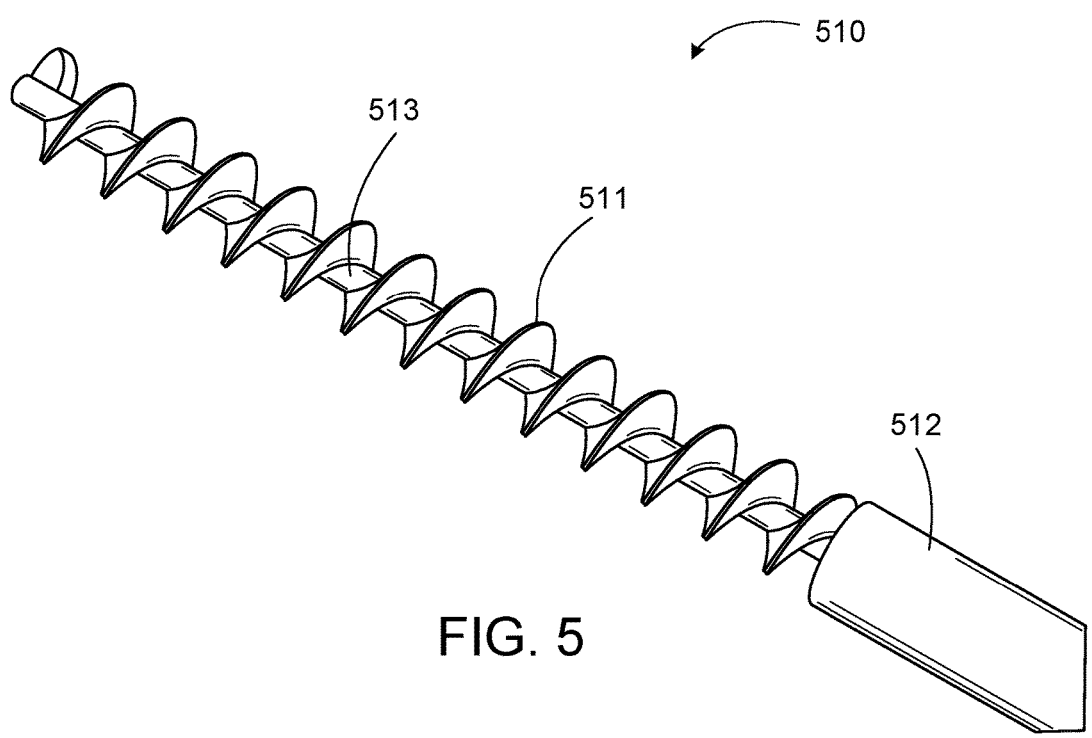
FIG. 5 depicts an embodiment of an inner member including an inner needle having a solid cylindrical core and helical ridge.

FIG. 5 depicts an embodiment of an inner member 512 including an inner needle 510 having a solid cylindrical core 513 and helical ridge 511. A therapeutic gel (not shown) is deposited on inner needle 510 between adjacent ridge portions by dipping inner needle 510 into a gel. Once the inner needle 510 is in place, it can be rotated during retraction to remove the distal tip from both tissue and the therapeutic gel.

Figure 6:
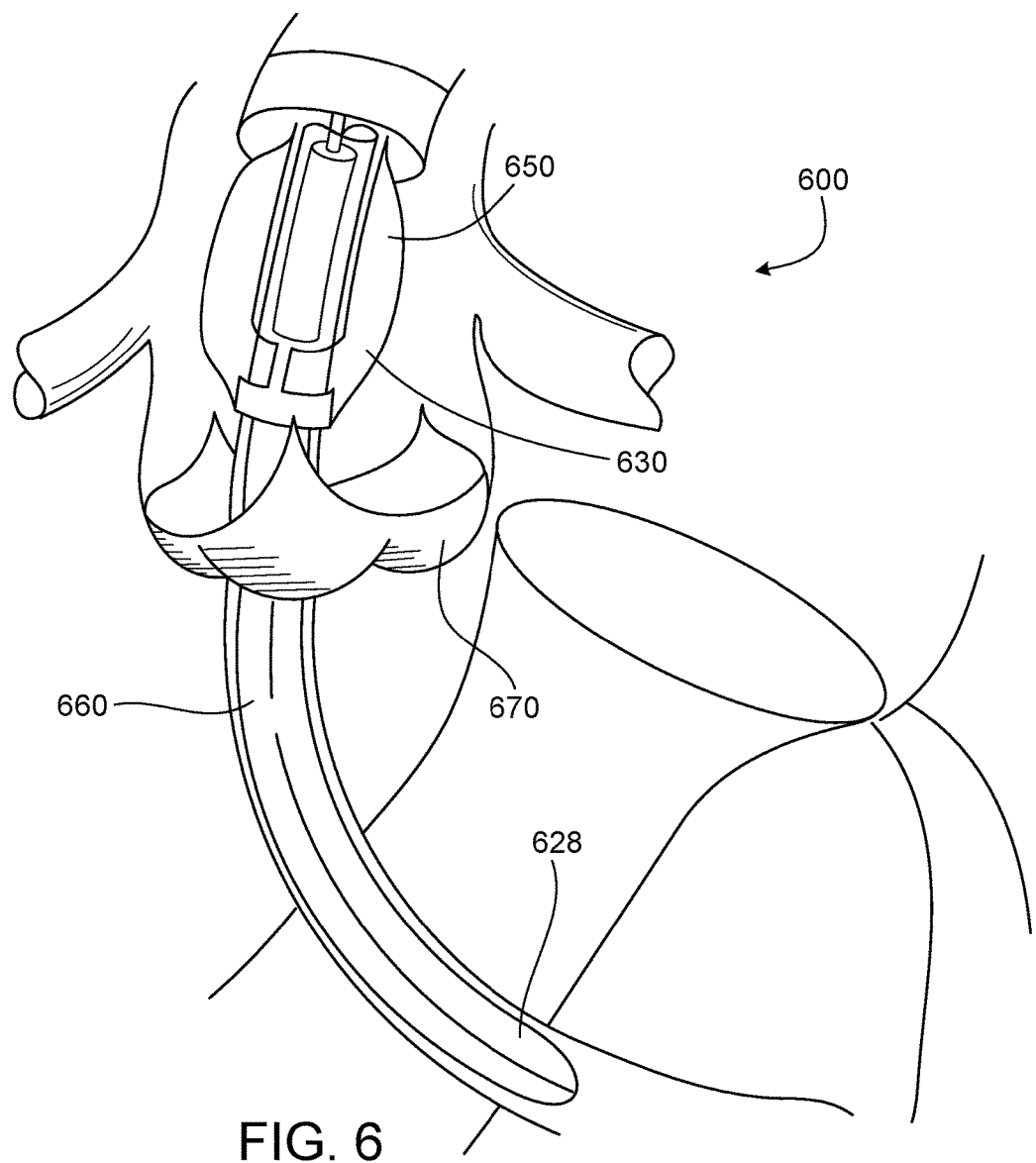
FIGS. 6, 7A, and 7B illustrate an example of an embodiment adapted to provide multiple deliveries of therapeutics. There is a gel reservoir stationed above aortic valve. Once the auger has delivered gel, it is retracted to this reservoir and reloaded.

FIG. 6 depicts an example of a system 600 arranged to allow the filling of the distal tip 628 with therapeutic 630 in situ, which can allow for multiple treatment locations without a need to fully remove the catheter system. As shown in FIG. 6, a reservoir 650 can be proximal to distal tip 628 such that it can be proximal to a heart valve 670 (e.g., the aortic valve). Between reservoir 650 and distal tip 628, steering guidewire and piston 660 can be located guide distal tip 628 to a desired location. One or more therapeutic agents 630 in reservoir 650 can be sequentially delivered to distal tip 628 by steering guidewire and piston 660.

Figures 7A, 7B:
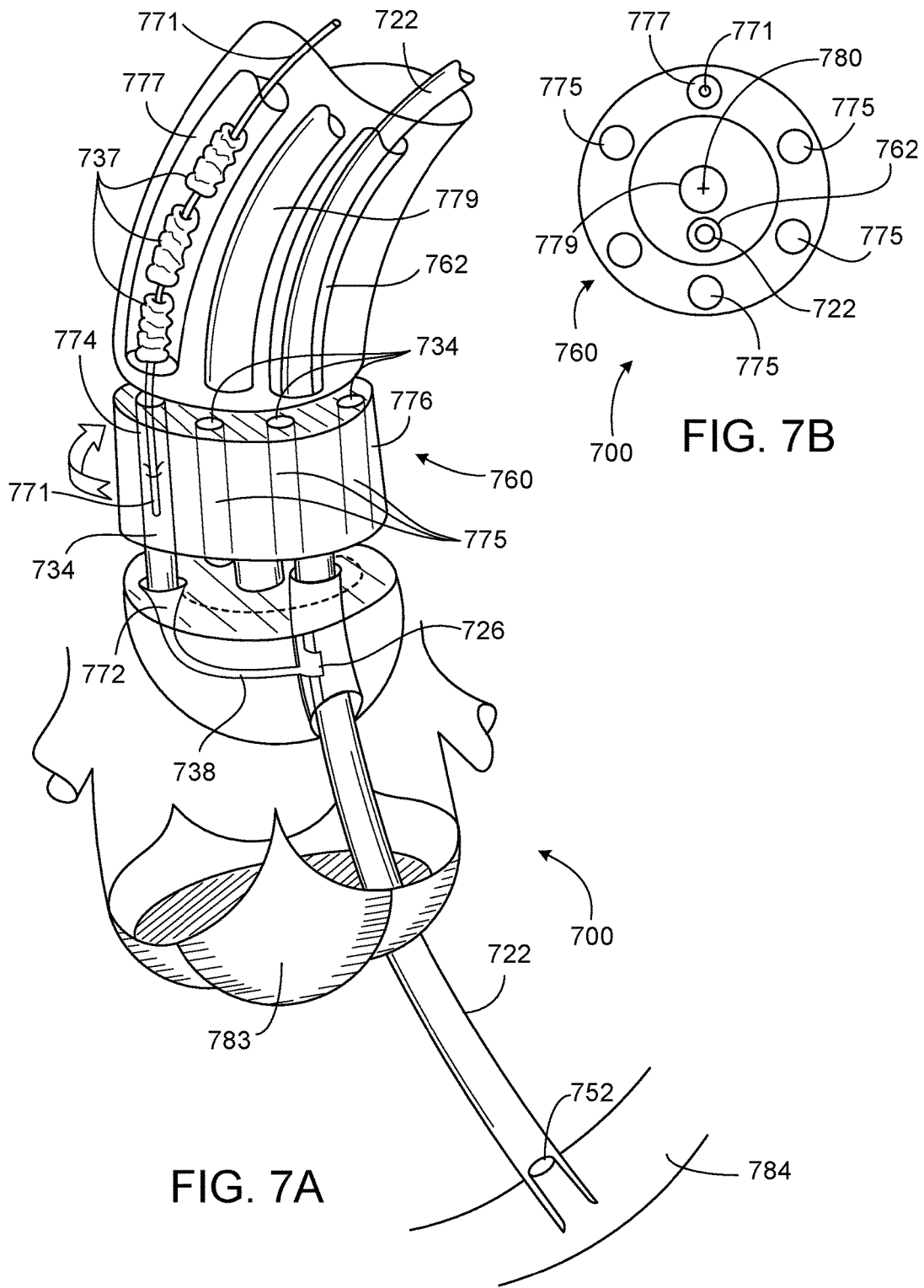

FIGS. 7A and 7B depicts an alternative arrangement for loading a catheter. As shown, system 700 may further include a loading catheter 760 including an injection catheter lumen 762, a carousel 776 for supplying therapeutic agent shells 734 held in reservoirs 775, a plunger lumen 777 for delivering a plunger 771 to crush shells 734 and collect spent shells 737, and a crusher drive lumen 779. As shown in FIG. 7B, carousel 776 can be rotated about an axis 780. Rotation of carousel 776 can be controlled via a control lumen 779. An outer member 722 can extend through injection catheter lumen 762 to reach a treatment location, such as left ventricular wall 784. A distal end 752 of outer member 722 be placed against treatment location tissue 784 to allow for therapeutic agent disposed between an inner helical needle (not shown) and an outer needle (not shown) to be inserted into the treatment location. During use, loading catheter 760 is advanced adjacent to aortic valve 783 Such that outer member 722 can extend through aortic valve 783 such that a distal end 752 of outer member 722 can be pressed against the left ventricular wall 784 so that a combination of an inner needle and an outer needle (not shown) can pierce ventricular wall 784. The outer needle (not shown) can then retracted, followed by a rotating retraction of inner needle (not shown) to leave a therapeutic gel in place.

After therapeutic gel is implanted at a first treatment location, system 700 can allow for the space between inner needle (not shown) and outer needle (not shown) to be refilled in situ. As shown in FIG. 7A, the distal tips of inner and outer needles can be retracted to a loading zone 726 in injection catheter lumen 762. Loading zone 726 is connected to an injection tube 738 for therapeutic gel to be injected around the inner needle. As shown, a portion of outer member 722 in loading zone 726 includes an aperture adapted to allow therapeutic gel (not shown) to pass through outer member 722 and around a helical inner needle (not shown). After therapeutic gel coats the inner needle, the inner needle can then be advanced through the outer member and outer member 722 to a second treatment location.

Therapeutic gel 730 injected around the inner needle (not shown) can be delivered to a distal end of loading catheter 760 by any suitable means. As shown in FIG. 7A, in some cases, shells 734 each encasing therapeutic gel can be supplied in carousel 776. A plunger 771 can cooperate with bottom crusher 772 to crush a shell 734 in a loading position 774. As shown, each shell 734 is advanced to the loading position 774 by rotating carousel 776. Plunger 771 can be pressed down to compress shell 734 such that plunger 771 pierces shell 734 such that therapeutic gel flows through injection tube 738 and into loading zone 726. Plunger 771 can additionally retain spent shells 737, such that each spent shell 737 is collected on the plunger 771. Rotation of carousel 776 can be actuated using any suitable drive system, which can access carousel via central lumen 779.

Figure 8A:
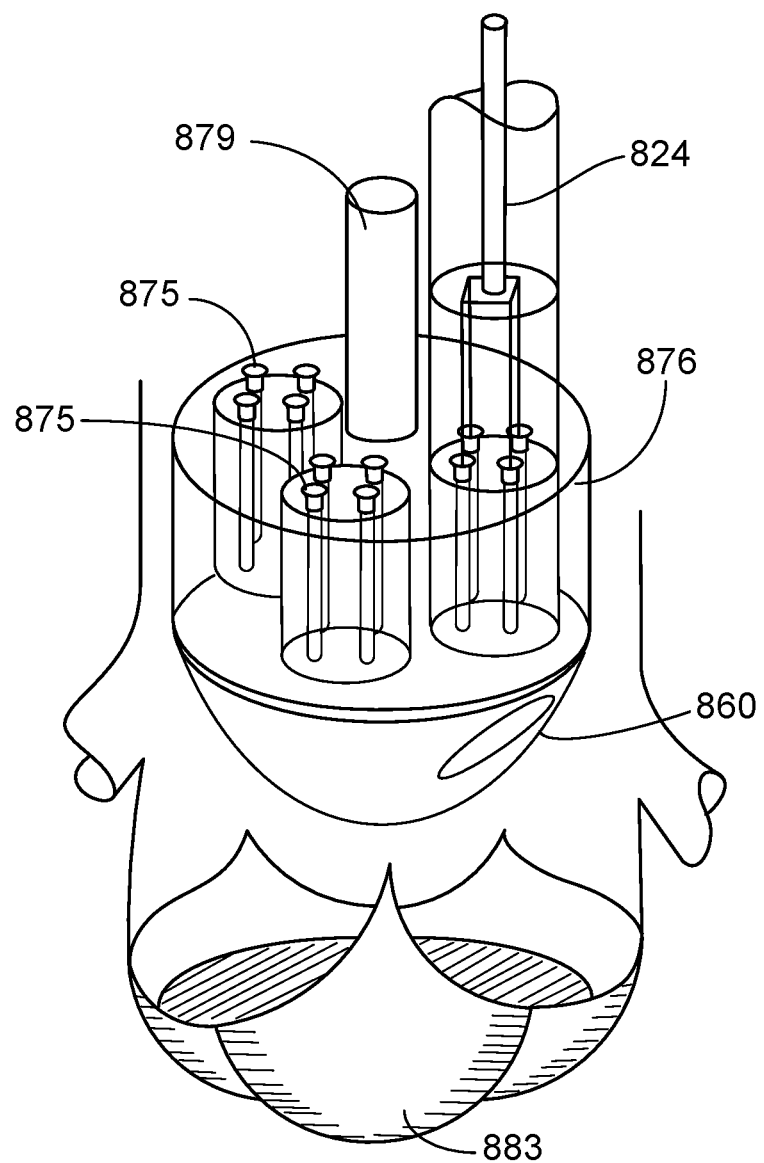
FIGS. 8A-8C and 9 depict a possible handle arrangement for an injection catheter system provided herein.
Figure 8B:
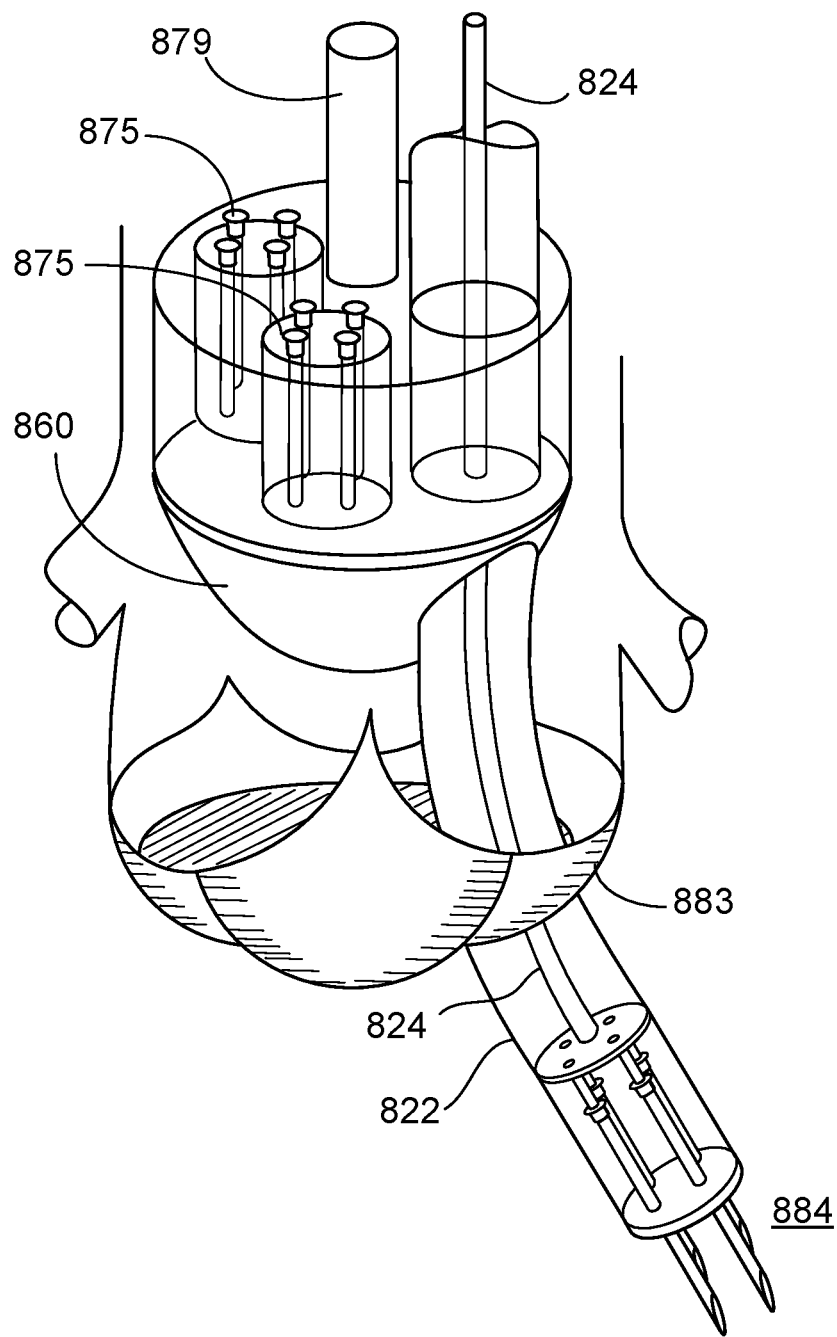
Figure 8C:
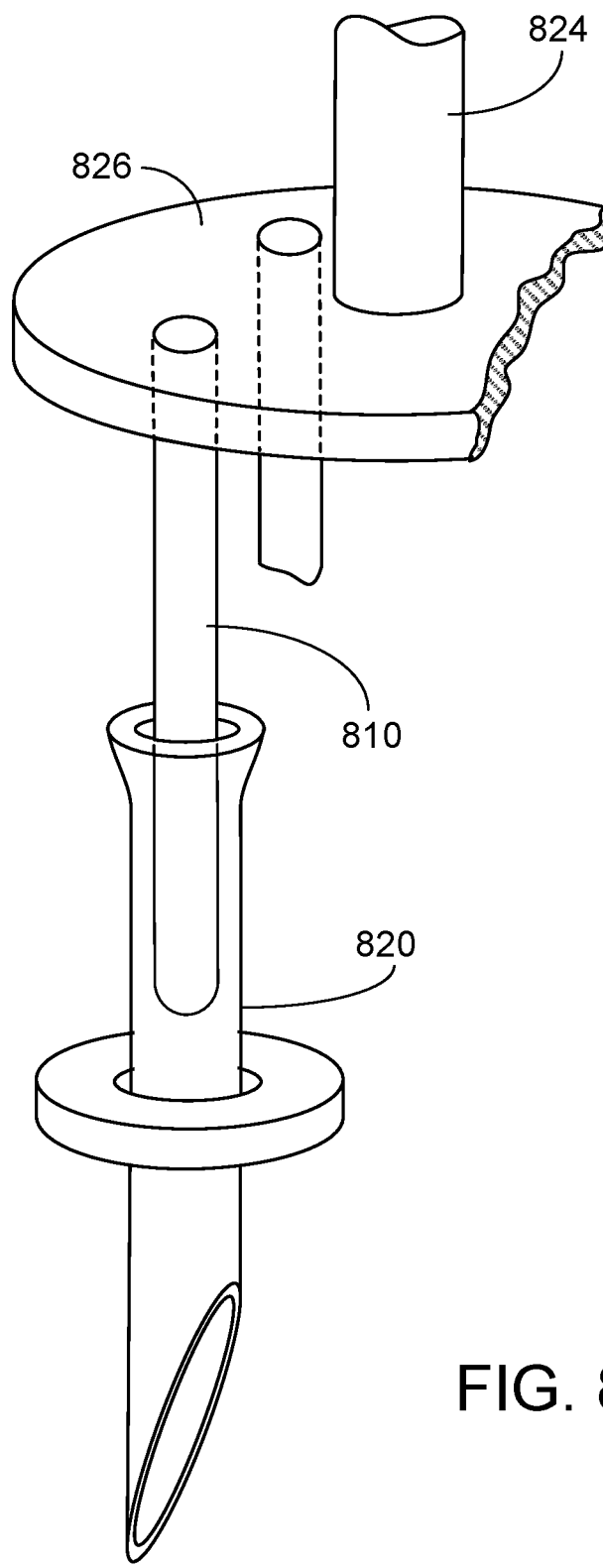

FIGS. 8A-8C depict an alternative loading arrangement where a rotatable carousel 876 rotates about a central rod 879 and includes a plurality of reservoirs 875 each housing a plurality of injection needle arrangements. Each needle arrangement can include an inner needle 810 and an outer needle 820, which can be inserted into target tissue 884 to produce deposits of therapeutic agent. Groups of inner and outer needles can be retained on plates 826 included in each reservoir 875. Plates 826 can be coupled sequentially to an actuator 824 by rotating carousel 876 and outer member 822 can be moved to abut different tissue locations between successive injections. When in use, a distal end of the loading catheter 860 can be delivered to a position adjacent to a valve 883 and outer member 822 can extend to a desired treatment location 884.

Figure 9:
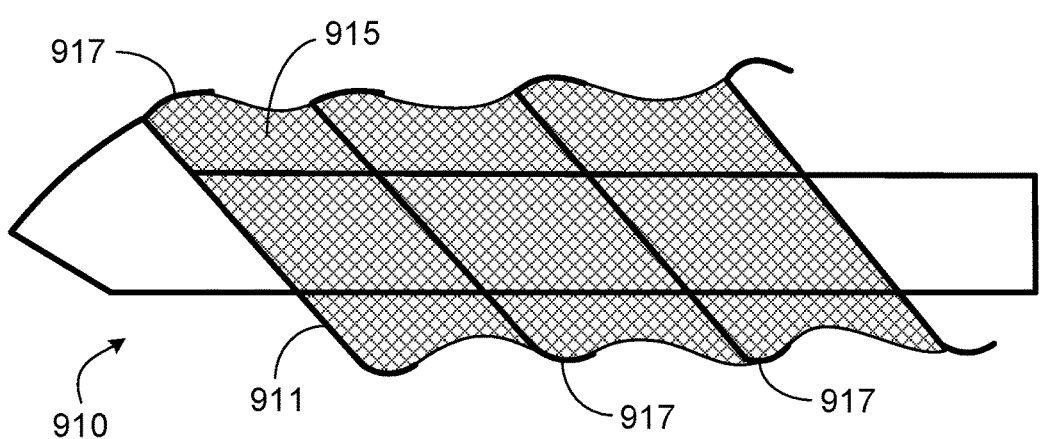

FIG. 9 depicts an embodiment of a single needle 910 that can be used to deliver therapeutic gel 915 held between spirals 911 without the use of an outer needle. Convex surface 917 can provide a convex surface facing a direction of entry to ease entry and prevent catching/snagging on the tissue.

Figure 10:
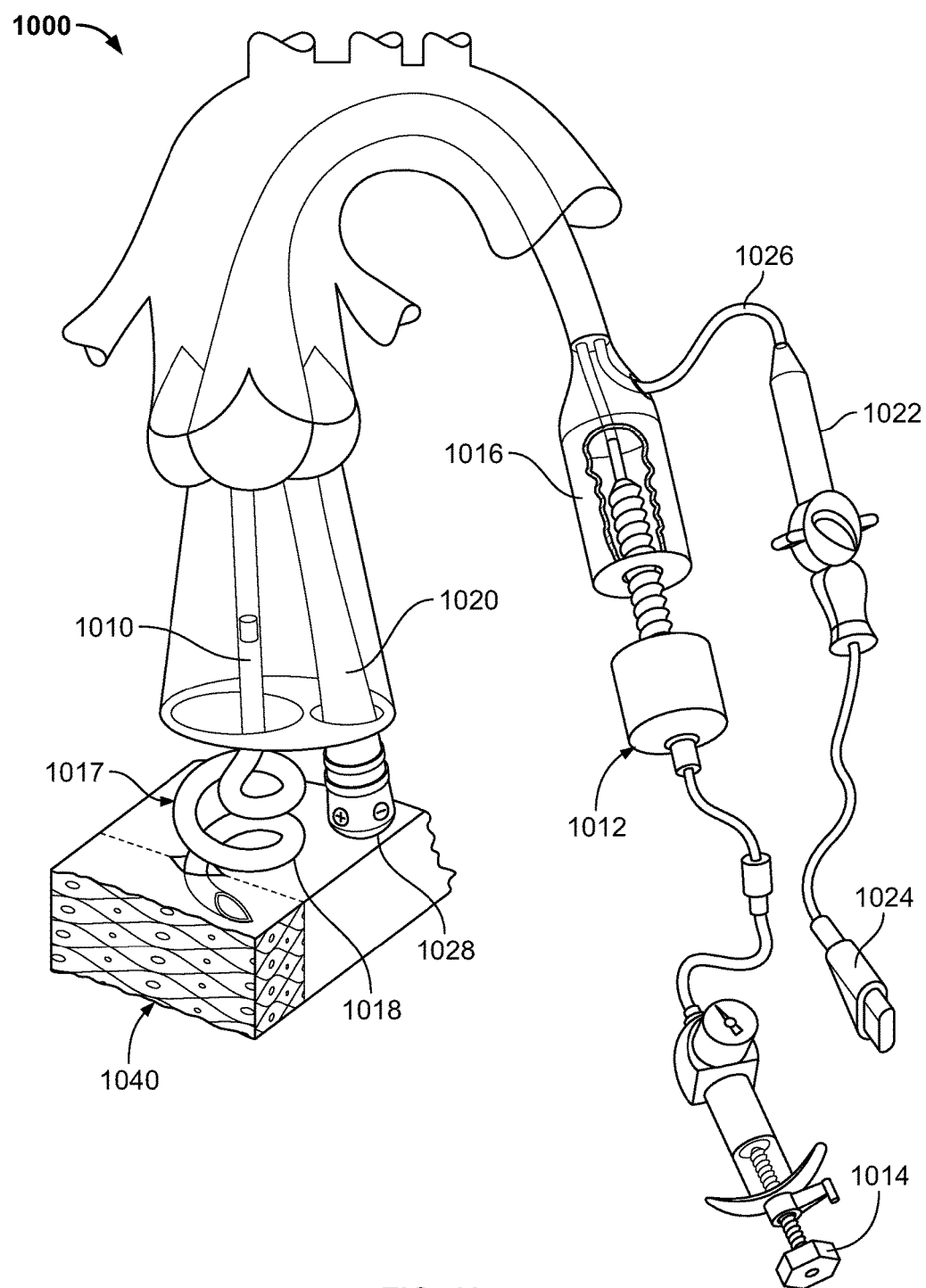

FIG. 10 depicts an example of a system 1000 arranged to allow the delivery of the therapeutics described herein with use of an injection device 1010 and an electrophysiology mapping device 1020 (e.g., INTELLA, RHYTHMIA). The depicted injection device 1010 can include a manifold portion 1012 containing a pneumatic pressurizing mechanism 1014 and an actuator 1016 for controlling needle injection depth. The manifold portion 1012 can be coupled to an elongate shaft that includes a distal portion 1017 with a helical needle 1018. The actuator 1016 can include a pumping screw that can be navigated within a single lumen or bi-lumen housing. As also shown in FIG. 10, the electrophysiology mapping device 1020 can include a handle portion 1022 with an interface connector 1024, and elongate shaft 1026 with a distal tip 1028 for detecting electrical activity in tissue. The electrophysiology device 1020 can be used to monitor electrical activity on a ventricular wall 1040 and to guide the delivery system 1000 to a site of low electric activity. The electrophysiology mapping device 1020 can be integrally coupled or detachably coupled to the injection device 1010. The system 1000 can deliver therapeutic agent deposits to the ventricular wall 1040 of a heart by advancing the distally loaded helical needle 1018 of the system 1000 while simultaneous identifying damaged wall tissue for stem cell injection at the distal tip 1028 of the electrophysiology mapping device 1020.

As shown in FIGS. 11A and 11B, the distal tip 1020 of the electrophysiology mapping device 1020 can include one or more electrodes 1030 to collect localized electrical recordings of a discrete tissue area. In some cases, the electrophysiology mapping device 1020 can optionally include an ablation tip containing a thermistor. The system 1000 provided herein can be arranged such that the distal tip 1028 of the electrophysiology device 1020 is positioned adjacent to the distal portion 1017 of the injection device 1010 to detect desired target sites prior to an injection and optionally monitor targeted tissue during the injection.

A number of embodiments of the invention have been described. Nevertheless, it will be understood that various modifications may be made without departing from the spirit and scope of the invention. For example, to aid in delivering the therapeutic gel to a specific treatment site of interest, the catheter injection system may be provided with a location device such as the IntellaTip MiFi™ XP available from Boston Scientific Corp. This device, which would be attached to the distal tip of the drug delivery catheter, features three mini-electrodes that provide accurate tip location and precise localized electrograms with minimal far-field effect. Accordingly, other embodiments are within the scope of the following claims.

What is claimed is:

1. A method of delivering a therapeutic gel to cardiac tissue, the method comprising
   (A) penetrating the cardiac tissue with an injection catheter comprising an outer needle comprising a tubular body defining a lumen and having a sharp, non-coring tip,
   the injection catheter further comprising an actuator and an inner needle at least partially disposed within the lumen of the outer needle, the inner needle having a distal tip defining a coil having an inner lumen configured to receive a guidewire, the distal tip configured such that at least a portion of the distal tip has a surface contour with an interstitial cavity in which a therapeutic gel is disposed,
   the outer and inner needles extending distally from the actuator,
   the distal tip being fully disposed within the lumen of the outer needle to temporarily retain the therapeutic gel in the interstitial cavity;
   (B) delivering the therapeutic gel to the cardiac tissue by proximally retracting the outer needle relative to the inner needle using the actuator to expose the therapeutic gel temporarily retained in the interstitial cavity to the cardiac tissue; and
   (C) after proximally retracting the outer needle, then releasing the therapeutic gel into the cardiac tissue by rotating and retracting the inner needle from the cardiac tissue.

2. The method of claim 1, wherein the surface contour of the inner needle is a spiral surface contour.

3. The method of claim 2, wherein actuating the actuator rotates the inner needle in a counterclockwise direction, releasing the therapeutic gel from the interstitial cavity of the inner needle having the spiral surface contour.

4. An injection catheter system comprising:
   (a) an actuator;
   (b) an outer needle comprising a sharp tip and a tubular body defining a lumen, the outer needle extending distally from the actuator; and
   (c) an inner needle at least partially disposed within the lumen and extending distally from the actuator, the inner needle having a distal tip defining a coil having an inner lumen configured to receive a guidewire, the distal tip configured such that at least a portion of the distal tip has an outer surface contour with an interstitial cavity adapted to receive a therapeutic gel;
   wherein the system is configured such that (a) in a first position, the distal tip is fully disposed within the lumen to temporarily retain the therapeutic gel in the interstitial cavity and (b) in a second position, the outer needle is retracted proximally, exposing the interstitial cavity to deliver the therapeutic gel to a target area in a body; and
   wherein the actuator is adapted to proximally or distally translate the outer needle such that translation of the outer needle is independent of translation of the inner needle.

5. The injection catheter system of claim 4, wherein the surface contour comprises a spiral configuration.

6. The injection catheter system of claim 4, wherein the surface contour comprises a helical configuration.

7. The injection catheter system of claim 4, wherein the surface contour comprises a non-cylindrical configuration.

8. The injection catheter system of claim 4, wherein the surface contour comprises a cross-shaped configuration.

9. The injection catheter system of claim 4, wherein at least a portion of the distal tip longitudinally tapers from a first cross-sectional area to a second cross-sectional area that is smaller than the first cross-sectional area.

10. The injection catheter system of claim 4, wherein the surface contour comprises a tapered cylindrical configuration.

11. The injection catheter system of claim 4, wherein the target area in the body is cardiac tissue.

12. The injection catheter system of claim 4, further comprising an outer sheath with a sheath lumen therethrough.

13. The injection catheter system of claim 12, further comprising a lead assembly disposed within the sheath lumen, the lead assembly comprising:
  (i) an elongate body having a proximal end portion and a distal end portion with a tip; and
  (ii) a plurality of electrodes disposed about the distal end portion for locating the tip within a patient's body;
  wherein the actuator is adapted to proximally or distally translate the lead assembly such that translation of lead assembly is independent of the translation of the outer needle and the translation of lead assembly is independent of the translation of the inner needle.

14. The injection catheter system of claim 13, further comprising a reservoir disposed within the sheath lumen, the reservoir adapted to receive a plurality of encapsulated forms of the therapeutic gel.

15. The injection catheter system of claim 14, wherein the reservoir is adapted to receive encapsulated forms of the therapeutic gel that are generally spherical shaped polymeric vesicles comprising a cavity filled with the therapeutic gel.

16. The injection catheter system of claim 15, wherein the reservoir comprises a piston adapted to release the therapeutic gel from the polymeric vesicle and deposit the therapeutic gel in the interstitial cavity.

17. An injection catheter system for delivering a therapeutic gel to cardiac tissue, the system comprising:
  (a) an actuator;
  (b) an outer needle comprising a sharp tip and a tubular body defining a lumen, the outer needle extending distally from the actuator; and
  (c) an inner needle at least partially disposed within the lumen and extending distally from the actuator, the inner needle having a distal tip defining a coil having an inner lumen configured to receive a guidewire, the distal tip configured such that at least a portion of the distal tip has a tapered, spiral shape with a spiral interstitial cavity adapted to receive a therapeutic gel;
  wherein the system is configured such that (a) in a first configuration, the distal tip is fully disposed within the lumen to temporarily retain the therapeutic gel in the interstitial cavity and (b) in a second configuration, the outer needle is retracted proximally to deliver the therapeutic gel to the cardiac tissue; and
  wherein the actuator is adapted to proximally or distally translate the outer needle such that translation of the outer needle is independent of translation of the inner needle.

18. The injection catheter system of claim 17, further comprising a reservoir disposed within the sheath lumen, the reservoir adapted to receive a plurality of encapsulated forms of the therapeutic gel.

19. The injection catheter system of claim 18, wherein the reservoir is adapted to receive encapsulated forms of the therapeutic gel that are generally spherical shaped polymeric vesicles comprising a cavity filled with the therapeutic gel.

* * * * *